United States Patent [19]

Marten et al.

[11] Patent Number: 5,054,483

[45] Date of Patent: Oct. 8, 1991

[54] TRACHEAL CANNULAS AND STENTS

[75] Inventors: Lewis H. Marten, Quincy; Charles Lane, Duxbury, both of Mass.

[73] Assignee: Hood Laboratories, Pembroke, Mass.

[21] Appl. No.: 527,032

[22] Filed: May 22, 1990

Related U.S. Application Data

[62] Division of Ser. No. 319,534, Mar. 6, 1989, Pat. No. 5,017,188.

[51] Int. Cl.5 ............................................. A61M 16/00
[52] U.S. Cl. ........................... 128/207.14; 128/200.26; 606/196; 623/9
[58] Field of Search ....................... 128/200.26, 207.14; 606/191, 196; 604/284; 623/1, 9, 11, 12

[56] References Cited

U.S. PATENT DOCUMENTS

| | | | |
|---|---|---|---|
| 3,137,299 | 6/1964 | Tabor | 623/9 |
| 3,605,751 | 9/1971 | Gulling | 128/207.14 |
| 3,721,233 | 3/1973 | Montgomery et al. | 128/207.14 |
| 4,269,184 | 5/1981 | Montgomery | 128/200.26 |
| 4,610,667 | 9/1986 | Pedicano et al. | 604/192 |
| 4,795,465 | 1/1989 | Marten | 623/9 |

FOREIGN PATENT DOCUMENTS

1405832  6/1988  U.S.S.R. .................. 623/9

*Primary Examiner*—Stephen C. Pellegrino
*Assistant Examiner*—Michael Rafa
*Attorney, Agent, or Firm*—Kane, Dalsimer, Sullivan, Kurucz, Levy, Eisele and Richard

[57] ABSTRACT

Disclosure is made of an improvement in the T-shaped tracheal stents and in the tracheal cannulas of the prior art, permitting one to conveniently have a complete and unitary unit including a closure member affixed to the device of the invention. Unidirectional retention sleeves are also described, which may be used in conjunction with the cannulas and the stents of the invention.

15 Claims, 5 Drawing Sheets

TRACHEAL CANNULAS AND STENTS

This is a divisional of co-pending application Ser. No. 319,534 filed on Mar. 6, 1989, U.S. Pat. No. 5,017,188.

BACKGROUND OF THE INVENTION

1. Field of the Invention

The invention relates to tracheal cannulas and to T-shaped tracheal stents.

2. Brief Description of the Prior Art

Tracheal cannulas, including T-shaped tracheal stents are well known in the prior art literature and have been described for example in U.S. Pat. Nos. 3,721,233; 4,269,184 and 4,795,465.

The present invention is an improvement in the art of tracheal cannulas and T-shaped tracheal stents which inherently include as a part thereof, a tracheal cannula component.

SUMMARY OF THE INVENTION

The invention comprises a tracheal cannula, which comprises;
 (A) a hollow tube having
  (i) a first open end for insertion within the trachea of a mammal through a tracheotomy incision;
  (ii) a second open end for communication with the atmosphere outside of said trachea, said second open end being adapted by size and configuration to be closed in a fluid seal with a closure means; and
  (iii) a tube body between the open ends, having inner and outer tube surfaces; and
 (B) a removable closure means adapted by size and configuration to close and form a fluid seal with the second open end of the hollow tube, said closure means having
  (i) attached handle means for gripping the closure means, said handle means being a perforated member, said perforation being adapted by size and configuration to receive therein the tubular body; and
  (ii) a severable stem, detachably connecting the handle means to the tube body.

The invention also comprises a T-shaped stent for insertion through a tracheotomy orifice into a trachea following surgical reconstruction of the cervical portion thereof, and surgical correction of tracheal and subglottic stenosis. The stent comprises an intraluminal tubular portion open at both ends and whose outside diameter is such as to provide a snugly fitting internal support for the reconstructed or corrected part of the trachea. An integral tracheotomy tubular portion of a diameter less than that of the intraluminal portion and disposed at an angle thereto intermediate the ends thereof and in communication with the interior of said intraluminal portion, is of a length to project outwardly through a tracheotomy orifice. After the disposition of the intraluminal portion within a trachea through the orifice, the junction of the two portions being ovate with its long axis lengthwise of the intraluminal portion and providing external flared shoulders lengthwise of both portions, provides, when the stent is in place, molding support of the margin or adjacent margins of the tracheal wall to overcorrect the margins and thereby to avoid the protrusion of any resulting scar tissue into the trachea. The stent is of resiliently yieldable stock enabling one end of the intraluminal portion to be folded against the tracheotomy portion or both ends thereof to be folded together for insertion and removal through the tracheotomy orifice. Removably attached to the outer wall of the tracheotomy tubular portion is closure means adapted by size and configuration to close and form a fluid seal with the distal open end of the tracheotomy tubular portion.

DETAILED DESCRIPTION OF THE PREFERRED EMBODIMENTS OF THE INVENTION

Those skilled in the art will gain an appreciation of the invention from a reading of the following description of preferred embodiments, when viewed in conjunction with the accompanying drawings of FIGS. 1 through 10, inclusive.

Figure 1:
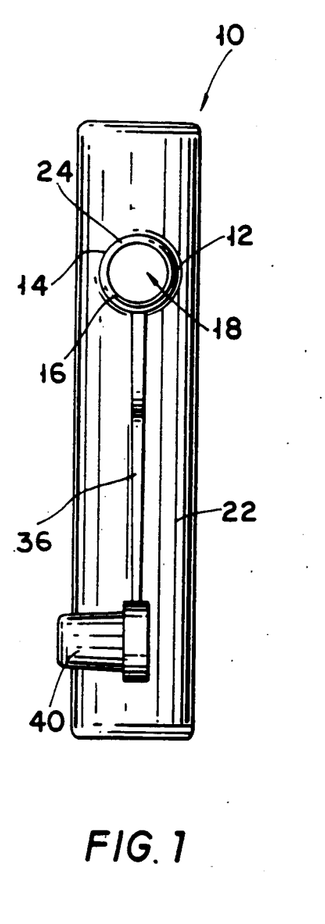
FIG. 1 is a front elevation of an embodiment T-shaped tracheal stent of the invention.
Figure 2:
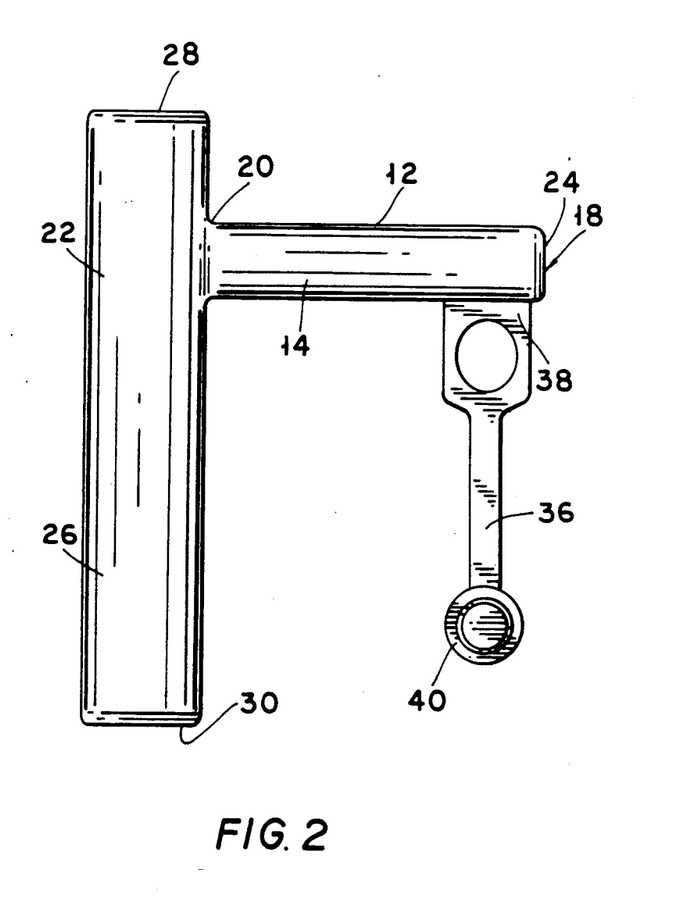
FIG. 2 is a side elevation of the embodiment tracheal stent shown in FIG. 1.

Referring first to FIG. 1, there is seen a front elevation of a preferred embodiment T-shaped tracheal stent 10 of the invention. The stent 10 comprises a tracheal cannula 12 portion. The cannula 12 portion is a tubular, hollow body having a smooth outer surface 14 and an inner surface 16 which defines the tube lumen 18. The lumen 18 is open and traverses the entire length of the cannula 12 portion. As may be seen more conveniently in FIG. 2, a side elevation of the embodiment stent 10 of the invention, the tracheal cannula 12 portion is integrally joined by a first end 20 to a tracheal stent 22 portion. The end 20 of cannula 12 portion is adapted by size and configuration to fit within the trachea of a mammal, through a tracheotomy incision. The opposite end 24 of cannula 12 portion is open to the atmosphere so that there is fluid communication through the length of lumen 18 between the atmosphere and the lumen of the hollow stent 22 portion, adapted to fit in a mammal's trachea. The stent 22 portion integrally joined to cannula 12 portion is likewise a hollow tubular element having a body 26, a first open end 28 and a second open end 30. The ends 24, 28, 30 are each, preferably, feathered to obviate a blunt end. The stent 22 portion of the stent 10 is adapted by size and configuration to fit within the trachea of a mammal. The outer surface 14 of the cannula 12 portion and the body 26 of the stent 22 portion is advantageously smooth and each is substantially uniform in diameter, throughout their respective lengths to avoid tissue granulation and physical distortion of a stoma, in use. The open ends 28, 30 of the stent 22 portion are open for fluid communication leading from the open end 24 of the cannula 12 portion and intervening lumen 18. There is an unobstructed pathway, facilitating periodic cleaning of the interior of stent 10, in place within in a trachea.

Although the stent 10 may be fabricated from any conventional material, the preferred embodiment stent 10 of the invention is advantageously molded from a medical grade (Food and Drug Administration approved) of yieldable stock material such as a silicone rubber, by known and conventional molding techniques. A silicone rubber is herein defined generally as a cross-linked silicone elastomer of the type vulcanized at room temperature (RTV) or at elevated temperatures (HTV). Dimethyl siloxanediol with silicone resin or alkyl silicate as cross-linking agents are typically used. Typically, fillers such as silica, calcium carbonate, titanium oxide and the like are normally added to the polymer formulation, usually by the manufacturer of the silicone polymer, as the filler materials provide degrees of rigidity and softness.

One example of a silicone rubber which may be used in the cannulas and the stents of the invention is Dow Corning 3110 RTV silicone rubber. This material can be cross-linked at room temperature with Dow Corning RTV catalyst No. 4. Other silicone rubber resins are well known and available commercially and techniques of molding them are well known to the artisan.

The physical structure of the stent 10 as described to this point herein is conventional as is its method of manufacture and the method of use; see for example the description given in U.S. Pat. No. 3,721,233 incorporated herein by reference thereto.

The same dimensions, angles of structure and surface features described in the U.S. Pat. No. 3,721,233 may be used in the present invention. The following describes the improvements of the present invention.

Figure 3:
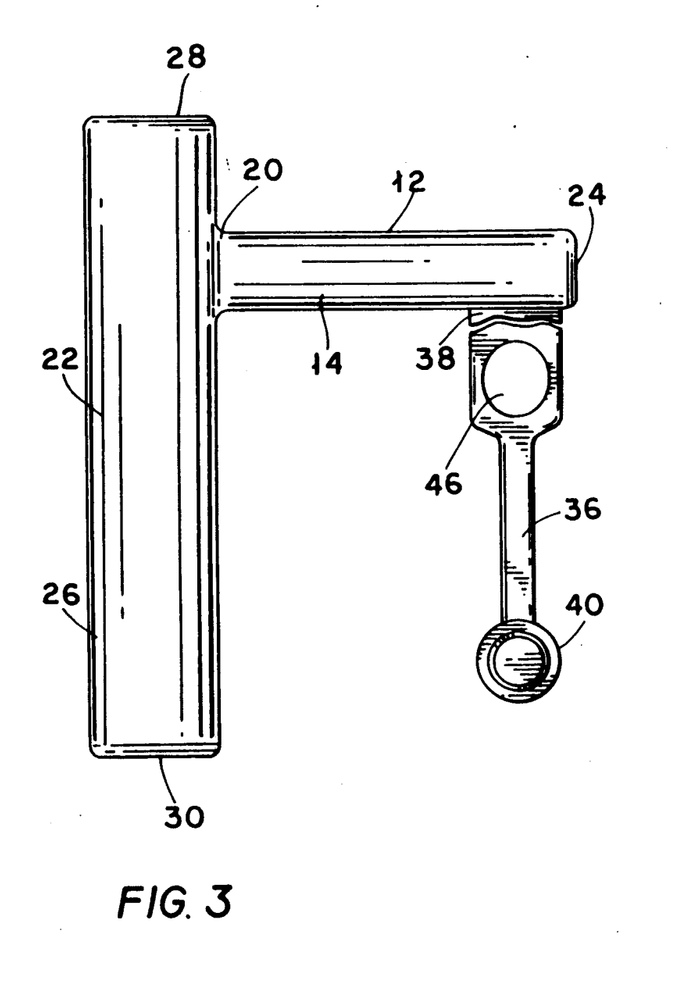
FIG. 3 is a view as in FIG. 2 but with one of the component members (handle) broken away.

Integrally formed in the fabrication of the stent 10 of the invention, and attached to the outer wall 14 of the cannula 12 portion is a handle 36 advantageously molded from the same material as the components 12, 22. Handle 36 projects perpendicular to and downward from cannula 12 portion and is attached to the outer surface 14 through means of a severable stem 38. Also connected to the handle 36 and distal from stem 38 is a closure means 40, advantageously a solid plug, adapted by size and configuration to removably close the open end 24 of the cannula 12 portion of the embodiment stent 10 of the invention. Advantageously the means 40 is a frusto-conical shaped solid plug molded to fit the open end 24 and form a fluid seal therewith. To use the closure means 40, by placement in a mating and sealing engagement within the open end 24, one may simply emplace the tethered closure means 40, in position in end 24, since the handle means 36 is advantageously thin enough and flexible enough to permit such movement. Alternatively, one may fracture or cut the stem 38 as shown in FIG. 3. The handle 36 then functions to facilitate emplacement of the closure means 40 within the open end 24, but is detached from its connection to the stent 10 as was shown in FIG. 1 and 2.

Figure 4:
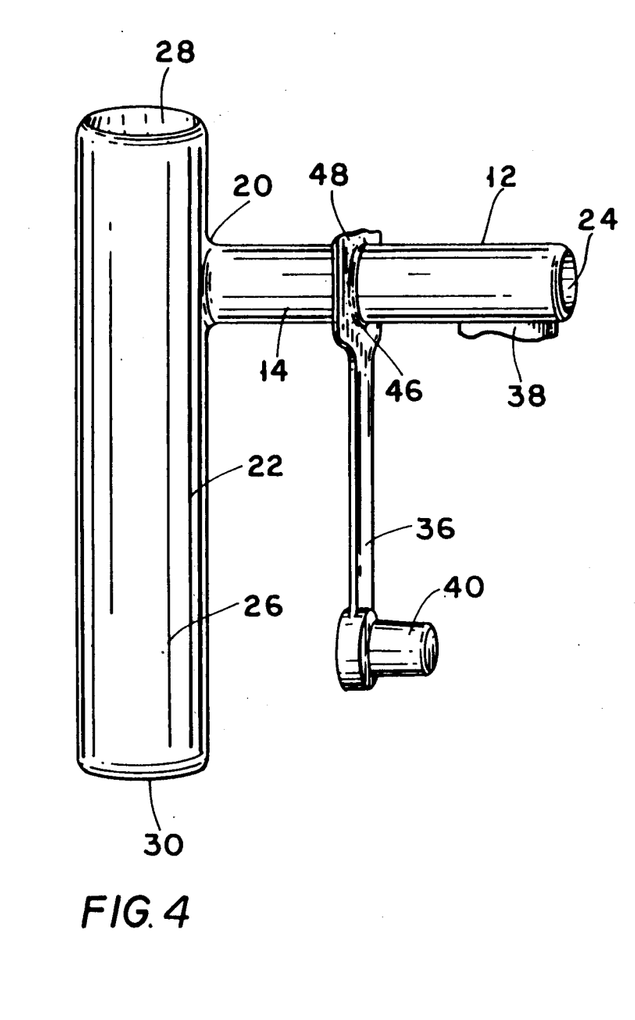
FIG. 4 is a view as in FIGS. 2 through 3, showing a reattachment of the handle means broken away in FIG. 3.

The handle means 36 which is advantageously a flexible flat band with a thickness of from about 0.05 to 0.10 inches also includes a slit or an aperture 46 therein, of a size and configuration adapted to permit one to insert the cannula 12 portion therein and slide the handle 36 means over the surface 14 of the cannula 12 portion of stent 10. Preferably, the aperture 46 is slightly smaller than the diameter of cannula 12 portion so that the edges of aperture 46 engage the surface 14 with a frictional fit, gripping the surface 14. This enables one to reattach the closure means 40 to the stent 10 of the invention as shown in FIG. 4, an illustration as in FIG. 3 but with the handle 36 movably reattached, removably, to the stent 10. In this position, assurance is provided that the closure means 40 will not be lost when it is removed from the open end 24, for cleaning of the stent 10 interiorally, or for other purposes. The flexible band of handle 36 permits one to move the closure 40 into the end 24 while reconnected to stent 10 by handle 36. It will be appreciated that the closure means 40 may be moved into a wide variety of positions when it is not emplaced in the end 24 of the stent 10, rotated on handle 36 about the outer surface 14 of the cannula 12 portion, without impairing the secure method of anchoring it to stent 10. The handle 36 is completely adjustable in respect to location on or with reference to the cannula 12 portion and can be moved along the length of the cannula 12 portion or rotated around it. This assures that one can move the closure means 40 into a wide variety of positions, out of the way of an operator working at the open end 24, without danger of misplacing the closure means 40. It is also completely detachable from the stent 10 if such is desirable.

Removable closures for tracheotomy tubes which are readily emplaced and removed by the patient or nursing staff have been a problem in the art. Too often, the closures are difficult to remove quickly and without causing momentary panic on the part of the patient. The present invention includes a new closure member which overcomes this problem of the art.

Figures 7, 8:
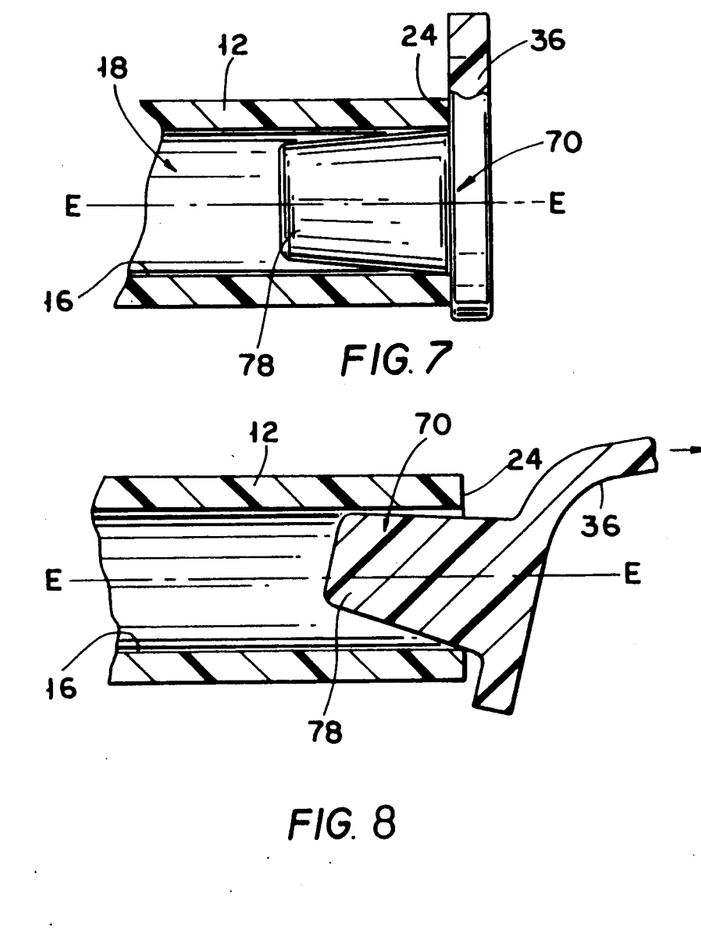
FIG. 7 is a cross-sectional view in part of an embodiment stent having an inserted closure means for the cannula component of FIGS. 1-4.
FIG 8 is a view as in FIG 7, showing partial removal of the closure means.

FIG. 7 is a view in perspective of an embodiment closure 70 closing the tracheotomy cannula 12 component portion (shown in cross-section) of the embodiment stent 10 shown in FIGS. 1-4. The closure 70 is a solid cylindrical plug having an outer flange (handle 36) disposed about the periphery of one end of the plug. The plug tapers from a maximum diameter at the handle 36 end to a minimum diameter at end 78. In addition, the end 78 may be outwardly feathered to facilitate insertion in end 24. The degree of taper is preferably within the range of from 1° to 5°, preferably about 3°. Preferably the length of closure 70 is within the range of from about 5 to about 15 millimeters. The material from which closure 70 is fabricated is preferably a synthetic polymeric resin having a smooth surface finish. Representative of such resins are polyethylene, polypropylene, polycarbonate, polysilicone and the like. The closure 70 may be fabricated in a size and configuration to sealingly nest within open end 24 of the tracheotomy cannula 12 component of stent 10 providing a fluid seal. The closure 70 is removably mounted within end 24 of cannula 12 when it is desired to close off the atmosphere from communication with lumen 18 of stent 10. For removal, one may grasp the handle 36 and exert an outward and biased pressure on the closure member 70, whereby it is misaligned with the axial line path E-E of lumen 18, thereby breaking surface contact between plug 78 and the inner wall 16 of the tracheotomy cannula 12; see FIG. 8. This misalignment of the closure member 70 within opening 24 facilitates its removal.

In a preferred embodiment stent 10 of the invention, the surface of the handle 36 in the zone 48 (on both sides of the handle 36) radiating outward from the periphery of the aperture 48, is a frictional surface. Representative of frictional surfaces are dimpled surfaces, abraded surfaces, knurled surfaces and like roughened surfaces. Such a frictional surface will be rolled or turned under when the handle 36 is moved along the longitudinal axis of the cannula 12 portion, since the aperture 46 is slightly less in diameter than the diameter of the cannula 12 portion. When turned or rolled under by the force of movement, the frictional surface 48 comes in contact with the smooth surface 14, providing drag or resistance to the dislocation of the handle 36 in respect to the cannula 12 portion. This dislocation resistance aids in the functioning of the handle 36 as a "stop" means to prevent the free end 24 of cannula 12 portion from disappearing into the patent's stoma should the stent 10 dislodge from its proper position in the trachea (more fully described below).

The handle 36 functions not only to support attachment of the closure means 40 to T-shaped stent 10 but prior to detachment can be used to assist in the placement of the stent 10 within the trachea of a mammal through a tracheotomy incision. The handle 36 with closure means 40 undetached or reattached to the cannula 12 portion of stent 10 as shown in FIG. 4 also functions to prevent the protruding end 24 of cannula 12 portion from disappearing into the patient's stoma if the stent 10 is accidentally dislodged from its proper position in the tracheotomy incision or stoma. The particular construction of the handle 36 as a flat strip facilitates this function, in contrast to, for example, a round or thread-like tether. There is another advantage associated with the stent 10 of the invention, not associated with prior art devices which have a closure means attached fixedly in place by a tether. The surgeon often desires to trim the length of the cannula 12 portion of a T-shaped stent, to accommodate the neck size of an individual patient. If he cuts back the length of a cannula 12 portion having no means of reattaching the tether, such as the handle 36, the closure means can not be conveniently reattached and the other functions of handle 36 can not be taken advantage of. The handle 36 can always be reattached to stent 10, after the cannula 12 portion is trimmed or cut-back in length.

Figure 5:
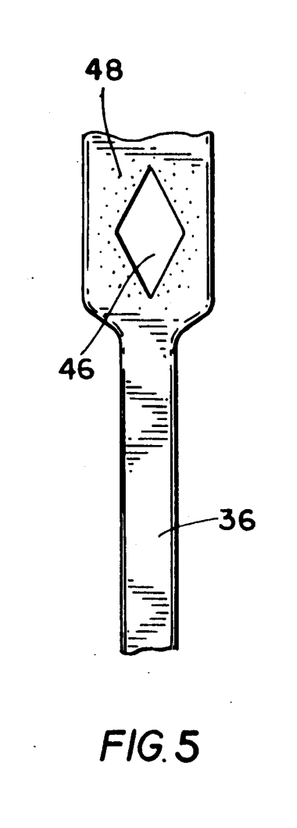
FIGS. 5 through 6 show alternate handle means for the embodiment T-shaped tracheal stent of FIG. 1.
Figure 6:
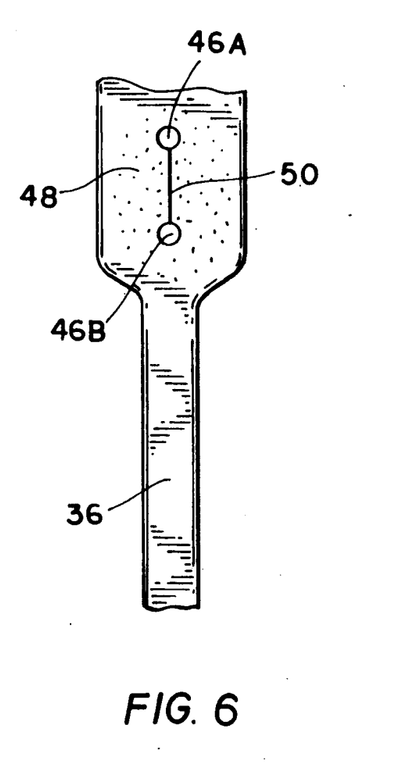

FIGS. 5 and 6 are drawings of alternate embodiment handle 36 components of the invention (partial views), showing that the aperture 46 may be of any design including a simple slit, the size and configuration of which is adapted to use as described above. In FIG. 5, a diamond shape aperture 46 is shown and in FIG. 6 two, small apertures 46A and 46B are joined by a slit 50. This is a particularly preferred aperture means, since each small perforation 46A and 46B functions to limit or prevent tearing of the handle 36 when the larger diameter cannula 12 portion is inserted through the slit 50 and the peripheral edges of the slit 50 roll under as previously described.

Although the invention has been described herein in relation to a stent 10, it will be appreciated that a number of modifications may be practiced without departing from the spirit and the scope of the invention. For example, the invention can be applied to the structure of a simple tracheal cannula (lacking the stent 22 portion). Whether used as a tracheal cannula or a T-shaped stent, the device of the invention is a unitary, single unit or assembly which is easily installed in the trachea.

The procedure for placement of the cannulas and stents of the invention is conventional and well known, being the same technique associated with prior art cannulas and stents; see for example the procedures described in the U.S. Pat. Nos. 3,721,233 and 4,269,184 incorporated herein by reference thereto. In general, after a tracheotomy incision has been made, the cannula or stent is simply inserted through the incision so one end is placed within the trachea and the other end protrudes out of the incision. In the case of a stent, the stent portion is folded in axial alignment with the tracheotomy cannula portion for insertion into the trachea where it resumes its normal T-shaped configuration. The cannula or stent is then fixed in the stoma with tape, suture or other means such as a ring washer secured to the tracheal cannula (see U.S. Pat. No. 4,269,184). This securing is to prevent inward or outward displacement of the device.

Figure 9:
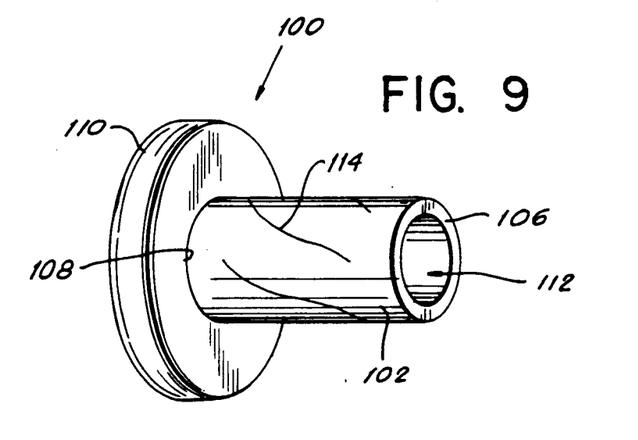
FIG. 9 is a view-in-perspective of an embodiment unidirectional retention sleeve used on the stent of the invention.

In a further embodiment of the invention, a unidirectional retention sleeve is fitted on the smooth outer surface 14 of the cannula 12 portion of stent 10 to prevent displacement of the cannula or stent of the invention from its position in the tracheotomy site. Referring to FIG. 9, there is seen a view-in-perspective of an embodiment unidirectional retention sleeve 100 of the invention which is advantageously fabricated from an elastomeric, synthetic polymeric resin such as a silicone rubber. The sleeve 100 consists of hollow tubular means 102 having a longitudinal axis. One end 106 of the tubular means 102 is open and adapted to receive in a low frictional sliding fit the cannula 12 portion of stent 10. The opposite open end 108 includes an integral flange 110, radiating outwardly from and perpendicular to the periphery of open end 108 to provide a stop and a finger grasping means. A lumen 112 traverses the interior of sleeve 100 from end 106 to end 108. A plurality of slits 114 penetrate the tubular means 102, providing closable entry into the lumen 112, about the outer periphery of the sleeve 100 between open ends 106, 108. Slits 114 function to activate a capturing means which cooperates with the tubular means 102 so as to allow axial sliding of the sleeve 100 on the cannula 12 portion of stent 10 in a low friction contact by a force applied in a first direction along the axis toward end 108; said capture means resisting the axial withdrawal therefrom in a second direction opposite the first direction. The capture means is capable of being overcome by a rotational force being placed on sleeve 100 about the longitudinal axis of the sleeve 100, during movement in the second direction.

Figure 10:
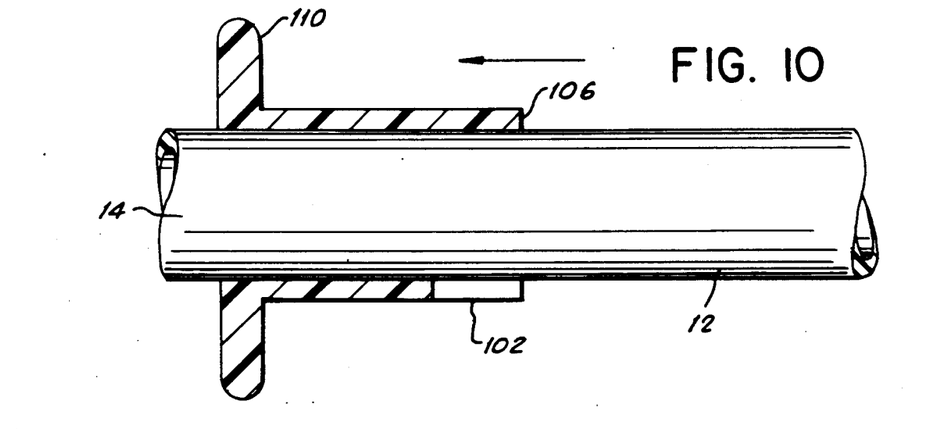
FIG. 10 is a view as in FIG. 9, showing operation of the retention sleeve on the cannula portion of the stent shown in FIGS. 1-4 (in cross-section).
Figure 11:
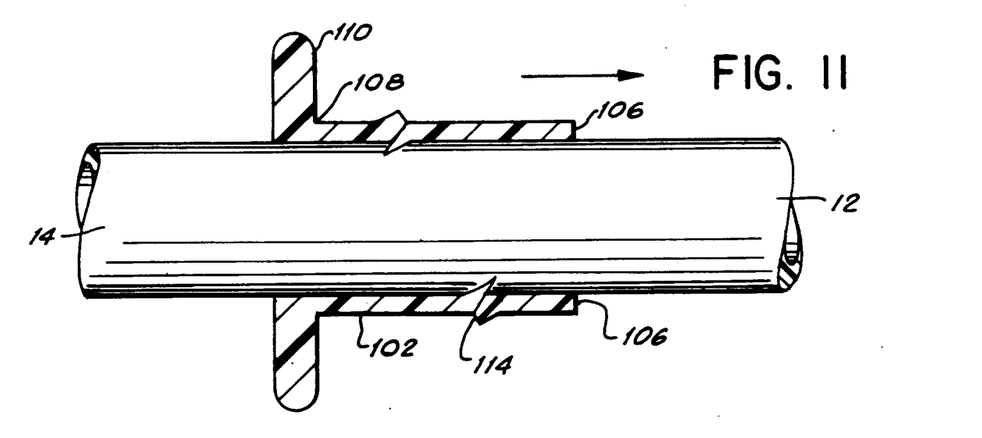
FIG. 11 is a cross-sectional view of the retention sleeve, as in FIG. 10, showing operation of the sleeve.

FIG. 10 is a cross-sectional side elevation of the embodiment sleeve 100 shown mounted on the surface 14 of the cannula 12 portion of stent 10. As may be seen from FIG. 10, the walls of lumen 112 of sleeve 100 forms with surface 14 a low friction sliding fit, snugly enough to form a slight or low frictional fit between the two components. In operation, the sleeve 100 may be moved freely in the direction of the arrow along surface 14 with a minimal force applied in that direction upon the flange 110. In this way, the sleeve 100 may be positioned upon surface 14 at any given and desired position relative to the tracheotomy incision. Moved snugly against the patient's throat, at the site of the incision, the sleeve 100 functions as a retainer means to hold the stent 10 in its position within the tracheotomy incision. When a force is applied in the opposite direction against the flange 110, the sleeve portion adjacent end 106 resists sliding sufficiently enough, relative to the sleeve portion adjacent end 108, for the sleeve portion or area of tubular means 102 between the slits 114 to buckle as shown in FIG. 11, a view as in FIG. 10 but with a force applied against flange 110 in an opposite direction (see arrow). The weakness of the zone between slits 114 causes buckling of the tubular means 102 as the portion of the tube adjacent to end 106 resists movement. This buckling, in turn, increases the frictional fit between tubular means 112 and surface 14 because of the increased drag and distortion of the tube means. This increase in friction and drag serves to resist the axial withdrawal of the sleeve 100 from its position on surface 14. The slits 114 and the intervening space serves as a "capture means" to hold sleeve 100 substantially in its position as a retainer. The slits 114 shown in the embodiment of FIGS. 9–11 are between the ends 106, 108. However, they may extend as far as the end 106 with the same functional use. Also, any number of slits may be spaced apart on the body of tubular means 102, as may be desired.

To remove the sleeve 100 from its mounting and use on the surface 14 of cannula 12 portion of the stent 10, one may withdraw the sleeve 100 as shown in FIG. 11, but with a simultaneous rotation of sleeve 100 either clockwise or counterclockwise. This rotational withdrawl of the sleeve 100 avoids a buckling of the zone lined with the slits 114. An easy removal of the sleeve 100 is thereby achieved, in contrast to withdrawal without rotation of the sleeve 100.

Those skilled in the art will appreciate that many modifications can be made to the above described preferred embodiments without departing from the spirit and the scope of the invention. For example, ridges may be placed on the sleeve 100 walls forming the lumen 112, to provide the low friction fit described above. Also, the retention sleeve 100 of the invention may be used as a retaining device on any tubular element, for example catheter tubes, indwelling cannulas, drainage tubes and the like.

Figure 12:
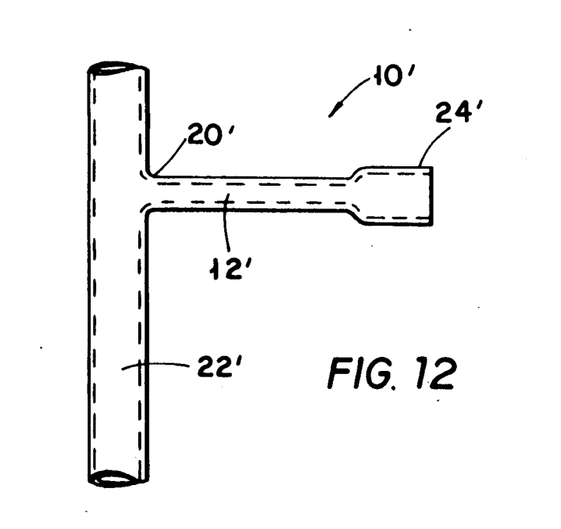
FIG. 12 is a side view of a stent as shown in FIGS. 1-4, but having a tracheostomy portion with an expanded diameter end.

Also, the tracheostomy portion (cannula 12) of stent 10 need not be uniform in diameter throughout its length from end 20 to end 24. The FIG. 12 is a side view of a stent 10', wherein structural elements similar to those found in stent 10 are similarly numbered, with the addition of a prime symbol. The stent 10' differs essentially from the stent 10 in that end 24 is of an expanded diameter. Advantageously, the end 24 increases in diameter (both inside and outside) by a factor of from 100 to 150 percent for a distance up to about 80 percent of the length of cannula 12 portion. The wider diameter of a portion of the cannula 12 portion will substantially decrease the possibility of dislodgement. Also, the larger closure for end 24 necessitated, facilitates manipulation and handling.

Figure 13:
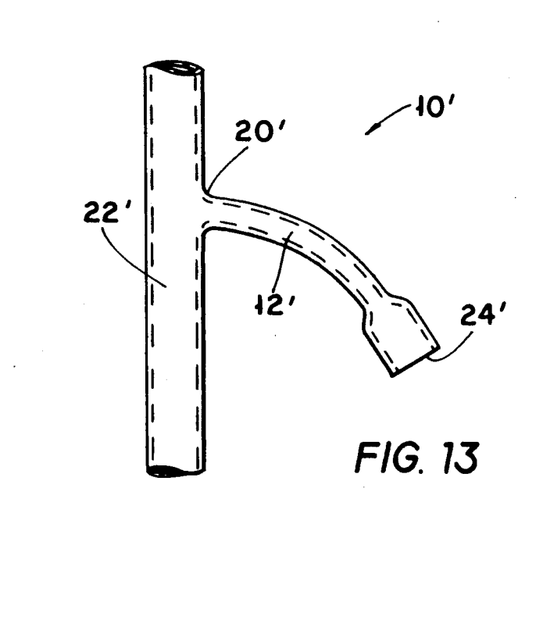
FIGS. 13-15, inclusive, are side views of alternate shaped stents of the invention.
Figure 14:
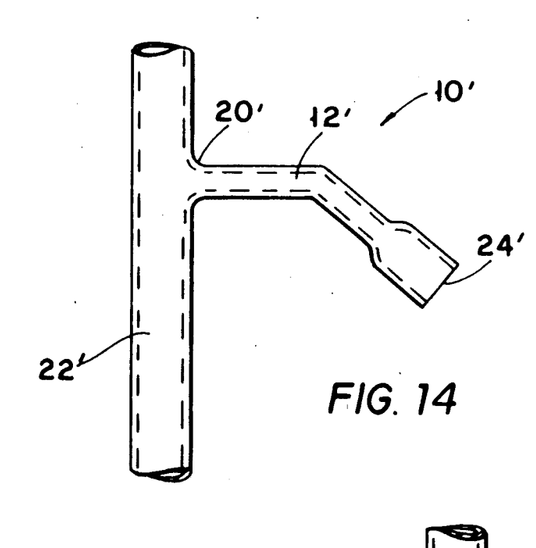
Figure 15:
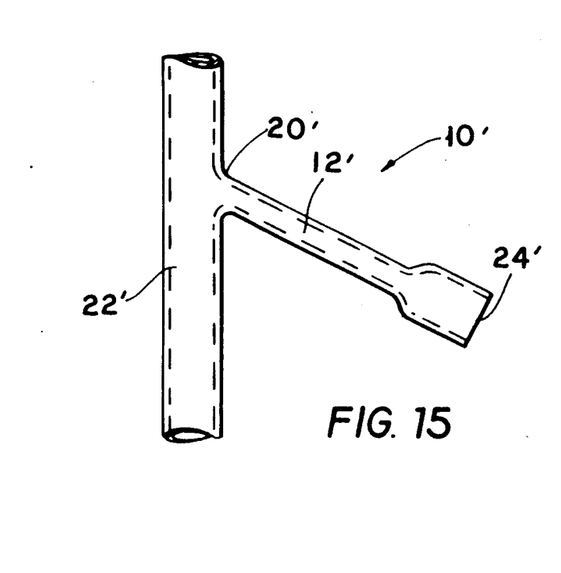

So to, the cannula 12' portion of stent 10' may be angled or curved in whole or part as shown in the accompanying drawings of FIGS. 13–15. FIGS. 13–15 are side views of alternate shaped stents 10' where the cannula 12 portion is curved or angled to accommodate specific patients such as infants and young children. Such shapes are anatomically correct for infants and children, who have little or small necks.

What is claimed is:
1. A tracheal cannula comprising:
  A. a hollow tube having
    (i) a first open end for insertion within the trachea of a mammal through a tracheotomy incision;
    (ii) a second open end for communication with the atmosphere outside said trachea, said second open end being adapted by size and configuration to be closed in a fluid seal; and
    (iii) a tube body between the open ends; and
  B. closure means integral with said hollow tube and having:
    (i) a severable stem frangibly attached to said hollow tube at a point adjacent to said second open end;
    (ii) a plug adapted by size and configuration to fit in said second open end to form a fluid seal therewith; and
    (iii) handle means for connecting said plug to said stem and for gripping the closure means, said handle means including a perforation adapted by size, and configuration to fit over said tube to hold the closure means on said tube body after separation from said tube, said handle means having a length selected to allow said plug to be inserted in said second open end without separating said stem from said tube.
2. A cannula of claim 1 fabricated in a unitary, single piece from a silicone rubber.
3. A cannula of claim 1 wherein the first open end is integrally joined to a stent portion, adapted by size and configuration to be received in the mammal's trachea.
4. A cannula of claim 1 wherein the tube body has a smooth outer surface.
5. A cannula of claim 1 wherein the surface of the handle disposed about the perforation is a friction surface.
6. A cannula of claim 5 wherein the perforation is of a size less than the diameter of the tube body.
7. A cannula of claim 1 wherein the handle is a cylindrical, oval or flat strip.
8. A cannula of claim 1 wherein the handle has two perforations joined together by a slit in the handle.
9. An assembly, which comprises;
  A. A tracheal cannula, which comprises a hollow tube having
    (i) a first open end for insertion within the trachea of a mammal through a tracheotomy incision;
    (ii) a second open end for communication with the atmosphere outside of said trachea, said second open end being adapted by size and configuration to be closed in a fluid seal with a closure means; and
    (iii) a tube body between the open ends, having a smooth outer tube surface and an inner tube surface defining an interior lumen traversing the tube body from first end to second end; and
  (B) a closure frangibly connected to said tube, means adapted by size and configuration to close and form a fluid seal with the second open end of the hollow tube, said closure means having handle means for gripping the closure means, said handle means being a perforated member, said perforation being adapted by size and configuration to receive therein in a frictional fit, the tube body.
10. The assembly of claim 9 wherein the closure means is a solid plug.
11. The assembly of claim 9 wherein the hollow tube is fabricated from a silicone rubber.

12. The assembly of claim 9 wherein the surface of the handle disposed about the perforation is a friction surface.

13. The assembly of claim 9 wherein there is a second perforation joined to the first perforation by a slit.

14. The assembly of claim 9 wherein the first open end is integrally joined to a stent portion, adapted by size and configuration to be received in a mammal's trachea through a tracheotomy incision.

15. A cannula of claim 9 wherein said handle means includes an aperture with a diameter smaller than the outer diameter of said tube body.

* * * * *